(12) United States Patent
Haskell-Luevano

(10) Patent No.: US 7,084,111 B2
(45) Date of Patent: Aug. 1, 2006

(54) MELANOCORTIN RECEPTOR TEMPLATES, PEPTIDES, AND USE THEREOF

(75) Inventor: Carrie Haskell-Luevano, Archer, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 334 days.

(21) Appl. No.: 10/602,394

(22) Filed: Jun. 23, 2003

(65) Prior Publication Data

US 2004/0260063 A1   Dec. 23, 2004

(51) Int. Cl.
    *A01N 37/18*   (2006.01)
(52) U.S. Cl. .................................................. 514/2
(58) Field of Classification Search ............... None
    See application file for complete search history.

(56) References Cited

U.S. PATENT DOCUMENTS

| | | | |
|---|---|---|---|
| 6,127,381 A | 10/2000 | Basu et al. | |
| 6,451,783 B1 | 9/2002 | Hadcock et al. | |

FOREIGN PATENT DOCUMENTS

| | | |
|---|---|---|
| WO | WO 99/21571 A1 | 5/1999 |
| WO | WO 99/54358 A1 | 10/1999 |
| WO | WO 01/74844 A2 | 10/2001 |
| WO | WO 02/18437 A2 | 3/2002 |
| WO | WO 03/006620 A2 | 1/2003 |

OTHER PUBLICATIONS

Tota, et al., Biochemitry, 1999, 38, 897-904.*

Han, G., J.M. quillan, K. Carlson, W. Sadee, V.J. Hruby (Feb. 27, 2003) "Design of Novel Chi8meric Melanotropin-Deltrophin Analogues. Discovery of the First Potent Human Melanocortin 1 Receptor Antagonist" *J. Med. Chem.* 46:810-819.

Joseph, Christine G., Andrzej Wilczynski, Jerry R. Holder, Zhimin Xiang, Rayna M. Bauzo, Joseph W. Scott, Carrie Haskell-Luevano (Dec. 2003) "Chimeric NDP-MSH and MTII melanocortin peptides with agouti-related protein (AGRP) Arg-Phe-Phe amino acids possess agonist melanocortin receptor activity" *Peptides* 24(12):1899-1908.

Szardenings, Michael et al. (Oct. 31, 1997) "Phage Display Selection on Whole Cells Yields a Peptide Specific for Melanocortin Receptor 1" *Journal of Biological Chemistry* 272(44):27943-27948.

Wilczynski, Andrzej, Xiang S. Wang, Christine G. Joseph et al. (Apr. 22, 2004) "Identification of Putative Agouti-Related Protein (87-132)-Melanocortin-4 Receptor Interactions by Homology Molecular Modeling and Validation Using Chimeric Peptide Ligands" *J. Med. Chem.* 47(9):2194-2207.

Bolin, K.A. et al. "NMR Structure of Minimized Human Agouti Related Protein Prepared by Total Chemical Synthesis" *FEBS Letters* 1999, pp. 125-131, vol. 451.

Castrucci, A.M.L. et al. "α-Melanotropin: The Minimal Active Sequence in the Lizard Skin Bioassay" *General and Comparitive Endocrinology*, 1989, pp. 157-163, vol. 73.

Hruby, V.J. et al., "α-Melanotropin: The Minimal Active Sequence in the Frog Skin Bioassay" *J. Med. Chem.*, 1987, pp. 2126-2130, vol. 30.

Holder, J. R. et al. "Structure-Activity Relationships of the Melanocortin Tetrapeptide Ac-His-DPhe-Arg-Trp-$NH_2$ at the Mouse Melanocortin Receptors. 1. Modifications at the His Position" *J. Med. Chem.*, 2002, pp. 2801-2810, vol. 45.

Holder, J. R. et al., "Structure-Activity Relationships of the Melanocortin Tetrapeptide Ac-His-DPhe-Arg-Trp-$NH_2$ at the Mouse Melanocortin Receptors: Part 2 Modifications at the Phe Position" *J. Med. Chem.*, 2002, pp. 3073-3081, vol. 45.

Jackson, P. J. et al. "Design, Pharmacology, and NMR Structure of a Minimized Cystine Knot with Agouti-Related Protein Activity" *Biochemistry*, 2002, pp. 7565-7572, vol. 41. No. 24.

(Continued)

*Primary Examiner*—Bruce R. Campell
*Assistant Examiner*—Satyanarayana R. Gudibande
(74) *Attorney, Agent, or Firm*—Saliwanchik, Lloyd & Saliwanchik

(57) ABSTRACT

The present invention relates to novel chimeric peptides and templates containing a combination of antagonist and agonist endogenous ligand residues. In particular, the present invention relates to novel chimeric peptides and templates thereof based upon melanocortin agonist peptides and agouti related protein (AGRP). The present invention provides multifunctional chimeric peptides having specific bioactivity at melanocortin receptors and their use as drugs to treat various diseases and conditions.

15 Claims, 1 Drawing Sheet

OTHER PUBLICATIONS

Kavarana, M. J. et al. "Novel Cyclic Templates of α-MSH Give Highly Selective and Potent Antagonists/Agonists for Human Melanocortin-3/4 Receptors" *J. Med. Chem.*, 2002, pp. 2644-2650, vol. 45.

Kiefer, L. L. et al. "Melanocortin Receptor Binding Determinants in the Agouti Protein" *Biochemistry*, 1998, pp. 991-997, vol. 37.

Kiefer, L. L. et al. "Mutations in the Carboxyl Terminus of the Agouti Protein Decrease Agouti Inhibition of Ligand Binding to the Melanocortin Receptors" *Biochemistry*, 1997, pp. 2084-2090, vol. 36.

Kim et al., "Hypothalamic Localization of thr Feeding Effect of Agouti-Related Peptide and α-Melanocyte-Stimulating Hormone," *Diabetes*, Feb. 2000, pp. 177-182, vol. 49.

Haskell-Luevano, C. et al., "Characterization of Melanocortin NDP-MSH Agonist Fragments at the Mouse Central and Peripheral Melanocortin Receptors" *J. Med. Chem.*, 2001, pp. 2247-2252, vol. 44.

Haskell-Luevano, C. et al. "The Agouti-Related Protein Decapeptide (Yc[CRFFNAFC]Y) Possesses Agonist Activity at the Murine Melanocortin-1 Receptor" *Peptides*, 2000, pp. 683-689, vol. 21.

Haskell-Luevano, C. et al. "Structure Activity Studies of the Melanocortin-4 Receptor by *in Vitro* Mutagenesis: Identification of Agouti-Related Protein (AGRP), Melanocortin Agonist and Synthetic Peptide Antagonist Interaction Determinants" *Biochemistry*, 2001, pp. 6164-6179, vol. 40.

McNulty, J. C. et al. "High-Resolution NMR Structure of the Chemically-Synthesized Melanocortin Receptor Binding Domain AGRP(87-132) of the Agouti-Related Protein" *Biochemistry*, 2001, pp. 15520-15527, vol. 40.

Al-Obeidi, F. et al. "Potent and Prolonged Acting Cyclic Lactam Analogues of α-Melanotropin: Design Based on Molecular Dynamics" *J. Med. Chem.* 1989, pp. 2555-2561, vol. 32.

Oosterom, J. et al. "Common Requirements for Melanocortin-4 Receptor Selectivity Unrelated Melanocortin Agonist and Endogenous Antagonist, Agouti Protein" *The Journal of Biological Chemistry*, Jan. 12, 2001, pp. 931-936, vol. 276, No. 2.

Perry, W. L. et al., "A Transgenic Mouse Assay for Agouti Protein Activity" *Genetics*, May 1995, pp. 267-274, vol. 140.

Perry, W. L. et al. "Coupled Site-Directed Mutagenesis/ Transgenesis Identifies Important Functional Domains of the Mouse Agouti Protein" *Genetics*, Sep. 1996, pp. 255-264, vol. 144.

Quillan, J. M. et al. "A Synthetic Human Agouti-Related Protein-(83-132)-$NH_2$ Fragment is a Potent Inhibitor of Melanocortin Receptor Function" *FEBS Letters*, 1998, pp. 59-62, vol. 428.

Sawyer, T. K. et al. "4- Norleucine, 7-D-Phenylalanine- $\Alpha$-Melanocyte-Stimulating Hormone: A Highly Potent -$\Alpha$-Melanotropin with Ultralong Biological Activity" *Biochemistry*, Oct. 1980, pp. 5754-5758, vol. 77, No. 10.

Tota, M. R. et al. "Molecualr Interaction of Agouti Protein and Agouti-Related Protein with Human Melanocortin Recptors" *Biochemistry*, 1999, pp. 897-904, vol. 38.

Willard, D. H.et al. "Agouti Structure and Function: Characterization of a Potent α-Melanocyte Stimulating Hormone Receptor Antagonist" *Biochemistry*, 1995, pp. 12341-12346, vol. 34.

Yang, Y-K. et al. "Functional Properties of an Agouti Signaling Protein Variant and Characteristics of its Cognate Radioligand" *Am. J. Physiol Regulatory Integrative Comp. Physiol.*, 2001, pp. R1877-R1886, vol. 281.

Yang, Y-K. et al. "Molecular Determinants of Ligand Binding to the Human Melanocortin-4 Receptor" *Biochemistry*, 2000, pp. 14900-14911, vol. 39.

Yang, Y-K. et al. "Characterization of Agouti-Related Protein Binding to Melanocortin Receptors" *Molecular Endocrinology*, 1999, pp. 148-155.

* cited by examiner

| Peptide | Primary sequence |
|---|---|
| α-MSH | Ac-Ser-Tyr-Ser-Met-Glu-His-Phe-Arg-Trp-Gly-Lys-Pro-Val-NH$_2$ |
| NDP-MSH | Ac-Ser-Tyr-Ser-Nle-Glu-His-DPhe-Arg-Trp-Gly-Lys-Pro-Val-NH$_2$ |
| MT-II | Ac-Nle-c[Asp-His-DPhe-Arg-Trp-Lys]-NH$_2$ |
| hAGRP (87-132) | CVRLHESCLGQQVPCCDPCATCYCRFFNAFCYCRKLGTAMNPCSRT |

MELANOCORTIN RECEPTOR TEMPLATES, PEPTIDES, AND USE THEREOF

GOVERNMENT SUPPORT

This invention was made with government support under a grant awarded from the National Institutes of Health under grant numbers DK57080 and DK64250. The government has certain rights in the invention.

FIELD OF THE INVENTION

The present invention relates to novel chimeric peptides and templates containing a combination of antagonist and agonist endogenous ligand residues. In particular, the present invention relates to novel chimeric peptides and templates thereof based upon melanocortin agonist peptides and agouti related protein (AGRP) antagonist peptide, and their use as drugs to treat various diseases and conditions.

BACKGROUND OF THE INVENTION

Today, about two-thirds of U.S. adults are overweight or obese, according to the Centers for Disease Control and Prevention. Obesity is harmful to physical health as well as an established risk factor for a number of potentially life-threatening diseases such as atherosclerosis, hypertension, diabetes, stroke, pulmonary embolism, and cancer. Moreover, obesity can wreak havoc on an individual's mental health and can affect a person's ability to interact socially with others.

Accompanying the devastating medical consequences of this problem is the severe financial burden placed on the health care system in the United States. The estimated economic cost of obesity and its associated illnesses from medical expenses and loss of income are reported to be in excess of $68 billion per year. Because of the impact of obesity on individuals and society, much effort has been expended to find ways to treat obesity, but little success has been achieved in the long-term treatment and/or prevention of obesity.

Pro-opiomelanocortin (POMC) derived peptides are known to affect food intake. Several lines of evidence support the notion that the G-protein coupled receptors (GPCRs) of the melanocortin receptor (MCR) family, several of which are expressed in the brain, are the targets of POMC derived peptides involved in the control of food intake and metabolism.

Five distinct MCRs have thus far been identified, and these are expressed in different tissues. MC1R was initially characterized by dominant gain of function mutations at the Extension locus, affecting coat color by controlling phaeomelanin to eumelanin conversion through control of tyrosinase. MC1R is mainly expressed in melanocytes. MC2R is expressed in the adrenal gland and represents the ACTH receptor. MC3R is expressed in the brain, gut, and placenta and may be involved in the control of food intake and thermogenesis. MC4R is uniquely expressed in the brain, and laboratory observations suggest that it is also involved in the control of food intake. See Kask A, et al., "Selective antagonist for the melanocortin-4 receptor (HS014) increases food intake in free-feeding rats," *Biochem. Biophys. Res. Commun.*, 245:90–93 (1998)). MC5R is expressed in many tissues, including white fat, placenta and exocrine glands. MC5R knockout mice reveal reduced sebaceous gland lipid production (Chen et al., "Exocrine gland dysfunction in MC5-R-deficient mice: evidence for coordinated regulation of exocrine gland function by melanocortin peptides," *Cell*, 91:789–798 (1997)).

Evidence for the involvement of MCRs in obesity includes: a) the agouti ($A^{vy}$) mouse which ectopically expresses an antagonist of the MC1R, MC3R and MC4R is obese, indicating that blocking the action of these three MCRs can lead to hyperphagia and metabolic disorders; b) MC4R knockout mice (Huszar, D. et al., "Targeted disruption of the melanocortin-4 receptor results in obesity in mice," *Cell*, 88:131–141 (1997)) recapitulate the phenotype of the agouti mouse—these mice are obese; c) the cyclic heptapeptide MT-II (a non-selective MC1R, MC3R, MC4R, and MC5R agonist) injected intracerebroventricularly (ICV) in rodents, reduces food intake in several animal feeding models (NPY, ob/ob, agouti, fasted) while ICV injected SHU-9119 (MC3R and MC4R antagonist; MC1R and MC5R agonist) reverses this effect and can induce hyperphagia; iv) chronic intraperitoneal treatment of Zucker fatty rats with an NDP-MSH derivative (HP228) has been reported to activate MC1R, MC3R, MC4R, and MC5R and to attenuate food intake and body weight gain over a 12-week period (Corcos, I. et al., "HP228 is a potent agonist of melanocortin receptor-4 and significantly attenuates obesity and diabetes in Zucker fatty rats," Society for Neuroscience abstracts, 23:673 (1997)).

A specific single MCR that may be targeted for the control of obesity has not yet been identified, although evidence has been presented that MC4R signaling is important in mediating feed behavior (Giraudo, S. Q. et al., "Feeding effects of hypothalamic injection of melanocortin-4 receptor ligands," *Brain Research*, 80:302–306 (1998)) and MC3R signaling may decrease food intake and participate in the regulation of energy homeostasis (obesity).

Agouti-related protein (AGRP) is a 132 (human) amino acid peptide putatively containing five disulfide bridges, and antagonizes the central brain melanocortin receptors (MC3R and MC4R) (Ollmann, M. M. et al., "Antagonism of central melanocortin receptors in vitro and in vivo by agouti-related protein," *Science*, 278:135–138 (1997); and Yang, Y. K. et al., "Characterization of Agouti-related protein binding to melanocortin receptors," *Mol. Endo.*, 13:148–155 (1999)). Agouti (ASP) is a homologue of AGRP and was first identified as an endogenous G-protein coupled receptor (GPCR) antagonist. Both of these proteins are the only known naturally occurring antagonists of GPCRs reported to date, making them a unique family of peptides.

Previous structure-activity studies of the agouti peptide identified the importance of the three amino acid motif Arg-Phe-Phe that is conserved in both agouti and AGRP (see, for example, Kiefer, L. et al., "Mutations in the carboxyl terminus of the agouti protein decrease agouti inhibition of ligand binding to the melanocortin receptors," *Biochemistry*, 36:2084–90 (1997)). These studies suggest that the conserved Arg-Phe-Phe motif found in both agouti and AGRP may be important for the antagonistic and molecular recognition properties of these two molecules at the melanocortin receptors.

All endogenous melanocortin agonists contain the putative amino acid sequence (His)/Phe-Arg-Trp, postulated to be important for melanocortin receptor molecular recognition and stimulation. Further extrapolation of the homology between the antagonist Arg-Phe-Phe motif and the endogenous melanocortin agonist conserved residues Phe-Arg-Trp, implies that the antagonist residues may be mimicking the agonist Phe-Arg-Trp interactions with the melanocortin receptors, as supported by Tota, M. R., et al., "Molecular interaction of Agouti protein and Agouti-related protein with human melanocortin receptors," *Biochemistry*, 38:897–904 (1999) and Haskell-Luevano, C., et al., "The agouti-related protein decapeptide (Yc[CRFFNAFC]Y) possesses agonist activity at the murine melanocortin-1 receptor," *Peptides*, 21:683–689 (2000).

Fragments of the agouti protein have been reported to be MC1R agonists (Yang, Y. K., et al., "Functional properties of an agouti signaling protein variant and characteristics of its cognate radioligand," *Am. J. Physiol. Regul. Integr. Comp. Physiol.*, 281:R1877–1886 (2001)). Various melanocortin agonist peptides (i.e., Ac-His-DPhe-Arg-Trp-NH$_2$ and Ac-His-Phe-Arg-Trp-NH$_2$) have been reported to possess nM and μM potencies, respectively, at the mouse melanocortin receptors, and that the tripeptide Ac-Phe-Arg-Trp-NH$_2$ possesses μM agonist activity at the mMC1R (Haskell-Luevano, C., et al., "Characterization of melanocortin NDP-MSH agonist peptide fragments at the mouse central and peripheral melanocortin receptors," *J. Med. Chem*, 44:2247–2252 (2001)). Further studies have shown that the Ac-His-Phe-Arg-Trp-NH$_2$ is the minimal fragment of melanocortin agonists required to produce a physiological response (μM) in the classic frog and lizard skin bioassay Hruby, V. J., et al., "alpha-Melanotropin: the minimal active sequence in the frog skin bioassay," *J. Med. Chem.*, 30:2126–2130 (1987); and Castrucci, A. M. L., et al., "Alpha-melanotropin: the minimal active sequence in the lizard skin bioassay," *Gen. Comp. Endocrinol*, 73:157–163 (1989).

In view of the need to better understand the biology of obesity and its relationship with MCRs, novel agents, methods, and compositions for treating or preventing obesity need to be identified and developed.

BRIEF SUMMARY OF THE INVENTION

The subject invention provides novel chimeric peptides based upon melanocortin agonist peptides and agouti related protein (AGRP) and methods for preparing such peptides. The chimeric peptides of the present invention are multi-functional and demonstrate specific bioactivity at melanocortin receptors.

In one embodiment of the subject invention, amino acids His/DPhe-Arg-Trp in melanocortin agonist peptides are replaced by the AGRP Arg-Phe-Phe resides to provide a potent multifunctional chimeric peptide that is active at melanocortin receptors. In another embodiment, chimeric peptides are provided in which AGRP Arg-Phe-Phe resides are substituted with the His/DPhe-Arg-Trp amino acids of melanocortin agonists peptides. In a related embodiment, the AGRP Arg-Phe-Phe domain of the chimeric peptides described herein can include natural and/or unnatural amino acids substituted within this domain. In a preferred embodiment, the endogenous disulfide bridge between cysteine amino acids may be substituted by asparagine and diaminopropionic acid side chains of AGRP resulting in the formation of a lactam bridge. All of these embodiments present multifunction chimeric peptides that are highly potent agonists and/or antagonists of melanocortin receptors.

BRIEF SUMMARY OF THE SEQUENCES

Figures 1, 2:
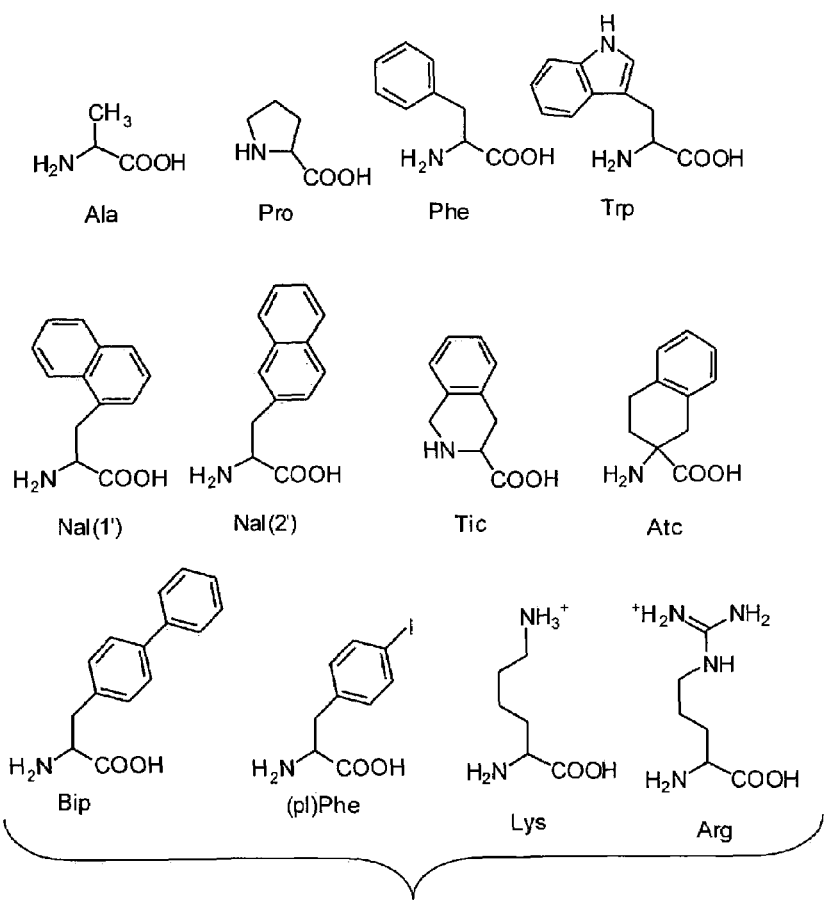
FIG. 1 is a summary of the amino acid sequences of certain melanocortin agonists and AGRP antagonist.
FIG. 2 are illustrations of amino acids and their abbreviations as described herein.

The synthesized peptides in accordance with the present invention are based either on an AGRP(109-118) template containing melanocortin based amino acid residues, on a melanocortin agonist template containing hAGRP(111-113) Arg-Phe-Phe amino acids, or on any of the templates or peptides discussed above containing a lactam bridge as opposed to a disulfide link. For purposes of experimentation and comparison, the peptides of SEQ ID NO: 1 (Tyr-c[Cys-Arg-Phe-DPhe-Asn-Ala-Phe-Cys]-Tyr); SEQ ID NO:2 (Tyr-c[Asp-Ala-Ala-Ala-Asn-Ala-Phe-Dpr]-Tyr); SEQ ID NO:12 (Ac-Ser-Tyr-Ser-Nle-Glu-His-Ala-Ala-Ala-Gly-Lys-Pro-Val); and SEQ ID NO:19 (Ac-Nle-c[Asp-His-Ala-Ala-Ala-Lys]) were synthesized. Peptides of the present invention include the following (from amino to carboxy terminal):

| | |
|---|---|
| Tyr-c[Asp-Arg-Phe-Phe-Asn-Ala-Phe-Dpr]-Tyr; | (SEQ ID NO:3) |
| Tyr-c[Asp-Trp-Arg-Phe-Asn-Ala-Phe-Dpr]-Tyr; | (SEQ ID NO:4) |
| Tyr-c[Asp-Trp-Arg-DPhe-Asn-Ala-Phe-Dpr]-Tyr; | (SEQ ID NO:5) |
| Tyr-c[Asp-Phe-Arg-Trp-Asn-Ala-Phe-Dpr]-Tyr; | (SEQ ID NO:6) |
| Tyr-c[Asp-DPhe-Arg-Trp-Asn-Ala-Phe-Dpr]-Tyr; | (SEQ ID NO:7) |
| Tyr-c[Asp-His-Arg-Phe-Phe-Asn-Ala-Phe-Dpr]-Tyr; | (SEQ ID NO:8) |
| Tyr-c[Asp-His-Phe-Arg-Trp-Asn-Ala-Phe-Dpr]-Tyr; | (SEQ ID NO:9) |
| Tyr-c[Asp-His-DPhe-Arg-Trp-Asn-Ala-Phe-Dpr]-Tyr; | (SEQ ID NO:10) |
| Ac-Ser-Tyr-Ser-Nle-Tyr-c[Asp-Arg-Phe-Phe-Asn-Ala-Phe-Dpr]-Tyr-Lys-Pro-Val; | (SEQ ID NO:11) |
| Ac-Ser-Tyr-Ser-Nle-Glu-Phe-Phe-Arg-Gly-Lys-Pro-Val | (SEQ ID NO:13) |
| Ac-Ser-Tyr-Ser-Nle-Glu-His-Phe-Phe-Arg-Gly-Lys-Pro-Val; | (SEQ ID NO:14) |
| Ac-Ser-Tyr-Ser-Nle-Glu-His-Arg-Phe-Phe-Gly-Lys-Pro-Val; | (SEQ ID NO:15) |
| Ac-Ser-Tyr-Ser-Nle-Glu-His-DArg-Phe-Phe-Gly-Lys-Pro-Val; | (SEQ ID NO:16) |
| Ac-Ser-Tyr-Ser-Nle-Glu-His-Arg-DPhe-Phe-Gly-Lys-Pro-Val; | (SEQ ID NO:17) |
| Ac-Ser-Tyr-Ser-Nle-Glu-His-Arg-Phe-DPhe-Gly-Lys-Pro-Val; | (SEQ ID NO:18) |
| Ac-Nle-c[Asp-His-Arg-Phe-Phe-Lys]; | (SEQ ID NO:20) |
| Ac-Nle-c[Asp-His-DArg-Phe-Phe-Lys]; | (SEQ ID NO:21) |
| Ac-Nle-c[Asp-His-Arg-DPhe-Phe-Lys]; | (SEQ ID NO:22) |
| Ac-Nle-c[Asp-His-Arg-Phe-DPhe-Lys]; | (SEQ ID NO:23) |
| Tyr-c[Asp-Ala-DPhe-Arg-Trp-Asn-Ala-Phe-Dpr]-Tyr; | (SEQ ID NO:24) |
| Tyr-c[Asp-His-Ala-Arg-Trp-Asn-Ala-Phe-Dpr]-Tyr; | (SEQ ID NO:25) |

```
                              -continued
Tyr-c[Asp-His-DPhe-Ala-Trp-Asn-Ala-    (SEQ ID NO:26)
Phe-Dpr]-Tyr;

Tyr-c[Asp-His-DPhe-Arg-Ala-Asn-Ala-    (SEQ ID NO:27)
Phe-Dpr]-Tyr;

Tyr-c[Asp-Pro-DPhe-Arg-Trp-Asn-Ala-    (SEQ ID NO:28)
Phe-Dpr]-Tyr;

Tyr-c[Asp-Phe-DPhe-Arg-Trp-Asn-Ala-    (SEQ ID NO:29)
Phe-Dpr]-Tyr;

Tyr-c[Asp-(rac)Atc-DPhe-Arg-Trp-Asn-   (SEQ ID NO:30)
Ala-Phe-Dpr]-Tyr;

Tyr-c[Asp-His-Pro-Arg-Trp-Asn-Ala-     (SEQ ID NO:31)
Phe-Dpr]-Tyr;

Tyr-c[Asp-His-(pI)DPhe-Arg-Trp-Asn-    (SEQ ID NO:32)
Ala-Phe-Dpr]-Tyr;

Tyr-c[Asp-His-DNal(2')-Arg-Trp-Asn-    (SEQ ID NO:33)
Ala-Phe-Dpr]-Tyr;

Tyr-c[Asp-His-DNal(1')-Arg-Trp-Asn-    (SEQ ID NO:34)
Ala-Phe-Dpr]-Tyr;

Tyr-c[Asp-His-DBip-Arg-Trp-Asn-Ala-    (SEQ ID NO:35)
Phe-Dpr]-Tyr;

Tyr-c[Asp-His-DPhe-Pro-Trp-Asn-Ala-    (SEQ ID NO:36)
Phe-Dpr]-Tyr;

Tyr-c[Asp-His-DPhe-Lys-Trp-Asn-Ala-    (SEQ ID NO:37)
Phe-Dpr]-Tyr;

Tyr-c[Asp-His-DPhe-Arg-Pro-Asn-Ala-    (SEQ ID NO:38)
Phe-Dpr]-Tyr;

Tyr-c[Asp-His-DPhe-Arg-Nal(2')-Asn-    (SEQ ID NO:39)
Ala-Phe-Dpr]-Tyr;

Tyr-c[Asp-His-DPhe-Arg-DNal(2')-Asn-   (SEQ ID NO:40)
Ala-Phe-Dpr]-Tyr;

Tyr-c[Asp-His-DPhe-Arg-Bip-Asn-Ala-    (SEQ ID NO:41)
Phe-Dpr]-Tyr;

Tyr-c[Asp-His-DPhe-Arg-Tic-Asn-Ala-    (SEQ ID NO:42)
Phe-Dpr]-Tyr;
and

Tyr-c[Asp-His-DPhe-Arg-Trp-Asn-Ala-    (SEQ ID NO:43)
DPhe-Dpr]-Tyr.
```

DETAILED DISCLOSURE OF THE INVENTION

The present invention pertains to novel chimeric multifunctional peptides that are biologically active at melanocortin receptors. The peptides of the present invention are based on the identification of AGRP and melanocortin agonist domains involved in binding to melanocortin receptors. Thus, the invention provides peptides with molecular structures that duplicate or mimic the binding domains of either AGRP or a melanocortin agonist.

Accordingly, the chimeric peptides of the present invention have either an AGRP template or an MCR agonist template. Preferably, the peptides containing the AGRP peptide template have melanocortin agonist-based bioactive determinant sequences that have been substituted for the corresponding, analogous AGRP template sequences. Alternatively, the peptides containing the MCR agonist template have AGRP-based bioactive sequences which have been substituted for the corresponding melanocortin agonist template sequences. In related embodiments, the AGRP-based bioactive sequences are substituted with natural and/or unnatural amino acids. In a preferred embodiment, the peptides of the present invention can have a lactam bridge replacing the disulfide link.

Definitions

The term "patient," describes an animal, including mammals, to whom treatment with the compositions according to the present invention is provided. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, rabbits, rats, mice, and ferrets; and domesticated farm animals such as cows, horses, swine, sheep.

As used herein, the term "peptide," is defined as an amino acid sequence from three amino acids to about 700 amino acids in length.

The term "AGRP/MCR agonist peptides" refers to the peptides having the amino acid sequence of any of SEQ ID NOS:4–7 and 9–10, together with all related peptides described herein. The AGRP/MCR agonist peptides may or may not have amino terminal methionines, depending on the manner in which they are prepared.

The term "NDP-MSH/AGRP peptides" refers to the peptides having the amino acid sequence of any of SEQ ID NOS:12–18, together with all related peptides described herein. The NDP-MSH/AGRP peptides may or may not have amino terminal methionines, depending on the manner in which they are prepared.

The term "MTII/AGRP peptides" refers to the peptides having the amino acid sequence of any of SEQ ID NOS: 20–23, together with all related peptides described herein. The MTII/AGRP peptides may or may not have amino terminal methionines, depending on the manner in which they are prepared.

Related peptides includes allelic variants; fragments; derivatives; substitution, deletion, and insertion variants; fusion polypeptides; and orthologs; and each amino acid of each such related peptide may be either natural or unatural of the "D" (natural) or "L" (unnatural) configuration which corresponds to the stereochemical designation "S" and "R," respectively, as defined in the RS system of Cahn et al., (*Pure Applied Chemistry*, 45:11–30 (1974), and references cited therein). Such related peptides may be mature peptides, i.e., lacking a signal peptide.

As used herein, the terms "AGRP/MCR agonist peptide variants," "NDP-MSH/AGRP peptide variants," or "MTII/AGRP peptide variants" refer to either AGRP/MCR agonist peptides, NDP-MSH/AGRP peptides, or MTII/AGRP peptides, respectively, whose amino acid sequences contain one ore more amino acid sequence substitutions, deletions, and/or additions as compared to the AGRP/MCR agonist peptide, NDP-MSH/AGRP peptide, or MTII/AGRP peptide amino acid sequences set forth in SEQ ID NOS:4–7, 9–10, 12–18, and 20–23. Such peptide variants containing amino acids of the natural L-configuration can be prepared from the corresponding nucleic acid molecule variants, which have a sequence that varies accordingly from the sequences encoding the peptides as set forth in SEQ ID NOS:4–7, 9–10, 12–18, and 20–23. Alternatively, such variants containing amino acids of the D-configuration (unnatural form) can be prepared synthetically using standard methods described herein (see also *Biochem. J.*, 219:345–373 (1984)).

The terms "AGRP/MCR agonist peptide derivatives," "NDP-MSH/AGRP peptide derivatives," or "MTII/AGRP peptide derivatives," as used herein, refer to peptides, variants or fragments thereof, that have been chemically modified, as for example, by addition of one or more water soluble polymers, N-linked or O-linked carbohydrates, sugars, phosphates, and/or other such molecules, where the molecule or molecules are not naturally attached to the peptides as set forth in SEQ ID NOS:4–7, 9–10, 12–18, and 20–23. Derivatives further include deletion of one or more chemical groups naturally attached to any of the peptides as set forth in SEQ ID NOS:4–7, 9–10, 12–18, and 20–23.

As used herein, the terms "AGRP/MCR agonist nucleic acid molecule," "NDP-MSH/AGRP nucleic acid molecule," or "MTII/AGRP nucleic acid molecule," when used to describe a nucleic acid molecule refer to a nucleic acid molecule or fragment thereof that encodes any of the peptides as set forth in SEQ ID NOS:4–7, 9–10, 12–18, and 20–23, and any fragments, derivatives, substitution, deletion, and insertion variants, fusion peptides, fusion polypeptides, and orthologs thereof.

The term "biologically active," as used herein refers to peptides that generate a functional (agonist and/or antagonist) pharmacological response at the melanocortin receptors.

For each amino acid, an additional conservative substitution includes the "homolog" of that amino acid, where the "homolog" is an amino acid with a methylene group ($CH_2$) inserted into the side chain at the beta position of that side chain. Examples of such homologs include, without limitation, homophenylalanine, homoarginine, homoserine, and the like.

The term "ortholog" refers to either AGRP/MCR agonist peptides, NDP-MSH/AGRP peptides, or MTII/AGRP peptides that correspond to AGRP/MCR agonist peptides, NDP-MSH/AGRP peptides, or MTII/AGRP, respectively, obtained from a species other than that from which a peptide of any of SEQ ID NOS: 4–7, 9–10, 12–18, and 20–23 was obtained.

In general, unless otherwise specified, the abbreviations used for the designation of amino acids and the protective groups used therefore are based on recommendations of the IUPAC-IUB Commission of Biochemical Nomenclature (*Biochemistry*, 11:1726–1732 (1972)). The nomenclature used to define compounds of the invention is that specified by IUPAC, published in *European Journal of Biochemistry*, 138:9–37 (1984). With regard to certain amino acids disclosed herein, their structures and abbreviations are provided in FIG. 2.

Therapeutic Compositions and Administration

Therapeutic compositions of AGRP/MCR agonist peptides, NDP-MSH/AGRP peptides, or MTII/AGRP peptides are within the scope of the present invention. Such compositions may comprise a therapeutically effective amount of the peptide or fragments, variants, or derivatives in admixture with a pharmaceutically acceptable carrier. Optionally, the peptide may be formulated in an acid-salt form. The carrier material may be water for injection, preferably supplemented with other materials common in solutions for administration to mammals such as, for example, alumina, lecithin, d-α-tocopherol, polyethyleneglycol, surfactants, serum proteins such as human serum albumin, phosphates, glycine, sorbic acid, and potassium sorbate.

Typically, a AGRP/MCR agonist peptide, NDP-MSH/AGRP peptide, or MTII/AGRP peptide therapeutic compound will be administered in the form of a composition comprising a purified peptide, fragment, variant, or derivative, optionally in its salt form, in conjunction with one or more physiologically acceptable carriers, excipients, or diluents.

Pharmaceutically acceptable salts of for the peptides of the present invention include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycolate, hemisulfate, hydrochloride, hydrobromide, hydroiodide, lactate, maleate, malonate, methanesulfonate, nicotinate, nitrate, oxalate, pectinate, phosphate, salicylate, succinate, sulfate, tartrate, thiocyanate, and other such pharmaceutically acceptable salts.

Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0–8.5, or acetate buffer of about pH 4.0–5.5, which may further include sorbitol or a suitable substitute therefor.

Any AGRP/MCR agonist peptide composition, NDP-MSH/AGRP peptide composition, or MTII/AGRP peptide composition can be administered parenterally. Alternatively, such compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of either AGRP/MCR agonist peptide compositions, NDP-MSH/AGRP peptide compositions, or MTII/AGRP peptide compositions useful for practicing the present invention may be prepared for storage by mixing the selected composition having the desired degree of purity with optional physiologically acceptable carriers, excipients, or stabilizers (*Remington's Pharmaceutical Sciences*, 18$^{th}$ Edition, A. R. Gennaro, ed., Mack Publishing Company (1990)) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the peptide composition(s) of the present invention to be employed therapeutically will depend, for example, upon the therapeutic objectives such as the indication for which the AGRP/MCR agonist peptide is being used, the route of administration, and the condition of the patient. Accordingly, it will be necessary for the therapist to titer the dosage and modify the route of administration as required to obtain the optimal therapeutic effect. A typical daily dosage may range from about 0.01 mg/kg to up to 1000 mg/kg or more, depending on the factors mentioned above. Typically, a clinician will administer the composition until a dosage is reached that achieves the desired effect. The composition may therefore be administered as a single dose, or as two or more doses (which may or may not contain the same amount of the peptide) over time, or as a continuous infusion via implantation device or catheter.

The peptide compositions of the subject invention to be used for in vivo administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accordance with known methods, i.e., oral, injection or infusion by intravenous, intraperitoneal, intracerebral (intraparenchymal), intracerebroventricular, intramuscular, intraocular, intraarterial, or intralesional routes, intranasal, or by sustained release systems or implantation device which may optionally involve the use of a catheter. Where desired, the compositions may be administered continuously by infusion, bolus injection or by implantation device.

Alternatively or additionally, the composition may be administered locally via implantation into the selected area using a membrane, sponge, or other appropriate material onto which a peptide of the subject invention has been absorbed.

Where an implantation device is used, the device may be implanted into any suitable tissue or organ, and delivery of AGRP/MCR agonist peptide, NDP-MSH/AGRP peptide, or MTII/AGRP peptide may be performed, directly through the device via bolus, or via continuous administration, or via catheter using continuous infusion.

According to the present invention, an AGRP/MCR agonist peptide, NDP-MSH/AGRP peptide, or MTII/AGRP peptide may be administered in a sustained release formulation or preparation. Suitable examples of sustained-release preparations include semipermeable polymer matrices in the form of shaped articles, i.e., films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22:547–556 (1983)), poly (2-hydroxyethyl-methacrylate) (Langer et al., *J. Biomed. Mater. Res.,* 15:167–277 (1981) and Langer, *Chem. Tech.,* 12:98–105 (1982)), ethylene vinyl acetate (Langer et al., supra) or poly-D(-)-3-hydroxybutyric acid (EP 133,988). Sustained-release compositions also may include liposomes, which can be prepared by any of several methods known in the art (i.e., Eppstein et al., *Proc. Natl. Acad. Sci. USA,* 82:3688–3692 (1985); EP 36,676; EP 88,046; EP 143,949).

The AGRP/MCR agonist peptides, NDP-MSH/AGRP peptides, or MTII/AGRP peptides, fragments, variants, and derivatives thereof, may be employed alone, together, or in combination with other pharmaceutical compositions. The peptides, fragments, variants, and derivatives of the subject invention may be used in combination with cytokines, hormones, growth factors, antibiotics, anti-inflammatories, and/or chemotherapeutic agents as is appropriate for the indication being treated.

Methods used for membrane encapsulation of cells are familiar to the skilled artisan, and preparation of encapsulated cells and their implantation in patients may be accomplished without undue experimentation. See, i.e., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975 (Baetge et al., CytoTherapeutics, Inc.). The cells, with or without encapsulation, may be implanted into suitable body tissues or organs of the patient.

As discussed above, it may be desirable to treat isolated cell populations such as, for example, brain cells and/or neurons with one or more peptides, variants, derivatives and/or fragments of the subject invention. This can be accomplished by exposing the isolated cells to the AGRP/ASP peptide, variant, derivative, or fragment directly, where it is in a form that is permeable to the cell membrane.

The following examples are intended for illustration purposes only, and should not be construed as limiting the scope of the invention in any way.

Abbreviations

The abbreviation "Boc" as used herein refers to tert-butyloxycarbonyl.

The abbreviation "DCM" as used herein refers to dichloromethane.

The abbreviation "Dde" as used herein refers to (1-(4,4-dimethyl-2,6-dioxocyclohex-1-ylidene)ethyl).

The abbreviation "DIPEA" as used herein refers to diisopropylethylamine.

The abbreviation "DMF" as used herein refers to dimethylformamide.

The abbreviation "DMSO" as used herein refers to dimethyl sulphoxide.

The abbreviation "EtOAc" as used herein refers to MeOH/ethyl acetate.

The abbreviation "Fmoc" as used herein refers to 9-fluorenylmethyloxycarbonyl.

The abbreviation "HOBt" as used herein refers to N-hydroxy-benzotriazole.

The abbreviation "MBHA" as used herein refers to methylbenzydryl-amine.

The abbreviation "PyBOP" as used herein refers to benzotriazole-1-yl-oxy-tris-pyrrolidino-phosphonium hexafluorophosphate.

The abbreviation "SPPS" as used herein refers to solid-phase peptide synthesis.

The abbreviation "tBu" as used herein refers to a tert-butyl group.

The abbreviation "TFA" as used herein refers to trifluoroacetic acid.

The abbreviation "TRH" as used herein refers to thyrotropin-releasing hormone.

The following examples illustrate procedures for practicing the invention. These examples should not be construed as limiting. All percentages are by weight and all solvent mixture proportions are by volume unless otherwise noted.

EXAMPLE 1—SYNTHESIS OF DISULFIDE CROSSLINKED OR CYCLIZED PEPTIDES

As understood by the skilled artisan, disulfide crosslinked or cyclized peptides can be synthesized using standard Fmoc methodology as described in Carpino, L. A., and Han, G. Y., "The 9-Fluorenylmethyoxycarbonsy Amino-Protecting Group," *J. Org. Chem.,* 37:3404–3409 (1972); and Chang, C., and Meienhofer, J., "Solid-phase peptide synthesis using mild base cleavage of N alpha-fluorenylmethyloxycarbonylamino acids, exemplified by a synthesis of dihydrosomatostatin," *Int. J. Pept. Protein Res.*, 11:246–249 (1978). Standard Fmoc methodology can be performed on an automated or semi-automated synthesizer (Advance ChemTech 440MOS or LabTech, Louisville, Ky.). The amino acids Fmoc-Ser(tBu), Fmoc-Tyr(tBu), Fmoc-Nle, Fmoc-Glu(OtBu), Fmoc-His(Trt), Fmoc-Arg(Pbf), Fmoc-DPhe, Fmoc-Trp(Boc), Fmoc-Gly, Fmoc-Lys(Boc), Fmoc-Pro, Fmoc-Val, and Fmoc-Phe are all commercially available. All reagents were ACS grade or better.

Peptides of the present invention were assembled on commercially available rink-amide-MBHA resin (0.40 meq/g substitution). The synthesis was performed using a 40 well Teflon reaction block with a course Teflon frit. Approximately 200 mg resin (0.08 mmole) was added to each reaction block well. The resin was allowed to swell for 2 hrs in dimethylformamide (DMF) and deprotected using 25% piperidine in DMF for 5 min followed by a 20 min 25% piperidine incubation at 500 rpms. A "Kaiser test," as described in Kaiser, E. et al., "Color Test for Detection of Free Terminal Amino Groups in the Solid-Phase Synthesis of Peptides," *Anal. Biochem.*, 34:595–598 (1970), was applied to the resin and yielded positive results. A positive Kaiser test indicates free amine groups on the resin.

The growing peptide chain was added to the amide-resin using the following general amino acid cycle: 500 μL DMF is added to each reaction well to "wet the frit," 3-fold excess amino acid starting from the C-terminus is added (500 μL of 0.5M amino acid solution containing 0.5M HOBt in DMF), followed by the addition of 500 μL 0.5M DIC in DMF and the reaction well volume is brought up to 3 mL using DMF. The coupling reaction is mixed for 1 hr at 500 rpms, followed by emptying of the reaction block by positive nitrogen gas pressure. A second coupling reaction is performed by the addition of 500 μL DMF to each reaction vessel, followed by the addition of 500 μL of the respective amino acid (3-fold excess), 500 μL 0.5M HBTU, 400 μL 1M DIEA, the reaction well volume is brought up to 3 mL with DMF, and mixed at 500 rpm for 1 hr. After the second coupling cycle, the reaction block is emptied and the resin-Nα-protected peptide is washed with DMF (4.5 mL 5 times). Nα-Fmoc deprotection is performed by the addition of 4 mL 25% piperidine in DMF and mixed for 5 min at 500 rpms followed by a 20 min deprotection at 500 rpms. The reaction well is washed with 4.5 mL DMF and the next coupling cycle is performed as described above.

Deprotection of the amino acid side chains and cleavage of the amide-peptide from the resin was performed by incubating the peptide-resin with 3 mL cleavage cocktail (95% TFA, 2.5% water, 2.5% triisopropylsilane) for 3 hrs at 500 rpms. The cleavage product was emptied from the reaction block into a cleavage block containing 7 mL collection vials under nitrogen gas pressure. The resin was washed with 1.5 mL cleavage cocktail for 5 min and 500 rpms and added to the previous cleavage solution. The peptides were transferred to pre-weighted 50 mL conical tubes and precipitated with cold (4°) anhydrous ethyl ether (up to 50 mL). The flocculent peptide was pelleted by centrifugation (Sorval Super T21 high speed centrifuge using the swinging bucket rotor) at 2000 rpm for 3 min, the ether was decanted off, and the peptide was washed one time with cold anhydrous ethyl ether and pelleted. The crude peptide was dried in vacuo 48 hrs. The crude peptide yields ranged from 60% to 90% of the theoretical yields. A 7 to 15 mg sample of crude peptide was purified by RPHPLC using a Shimadzu chromatography system with a photodiode array detector and a semi-preparative RP-HPLC $C_{18}$ bonded silica column (Vydac 218TP1010, 1.0×25 cm) and lyophilized. The purified peptide was >95% pure as determined by analytical RP-HPLC and had the correct molecular mass.

Disulfide bridge cyclization of the peptides synthesized above was performed in solution according to known methods, such as those described in Haskell-Luevano, C. et al., "The agouti-related protein decapeptide (Yc[CRFFNAFC]Y) possesses agonist activity at the murine melanocortin-1 receptor," *Peptides*, 21:683–689 (2000); and Haskell-Luevano, C. et al., "Design, synthesis, biology, and conformations of bicyclic alpha-melanotropin analogues,"*J. Med. Chem.*, 38:1736–1750 (1995).

The crude linear peptide (synthesized in Example 1 above) is dissolved in 20 mL of water and 3 mL of methanol. An oxidizing solution consisting of 200 mL 0.01M potassium ferricyanide, 10 mL saturated ammonium acetate, 20 mL acetonitrile, 10 mL water, was adjusted to pH=8.5 with a few drops of concentrated ammonium hydroxide. The peptide solution was taken up in a 50 mL syringe and transferred to the oxidizing solution via a syringe pump at a rate of 1.5 mL/h. When the transfer was complete, the pH was adjusted to 4.5 with glacial acetic acid. Amberlite resin (IRA-68 HCl form) was added to the mixture and left to mix for 45 min. The Amberlite resin was filtered off, with the solution containing the peptide concentrated, lyophilized, and purified by RP-HPLC.

EXAMPLE 2—SYNTHESIS OF PEPTIDES CONTAINING CYCLIC LACTAM BRIDGE

In accordance with the present invention, peptides containing cyclic lactam bridges can be prepared using standard Boc methodology as described in Merrifield, R. B., "Solid Phase Synthesis. II. The Syntheis of Bradykinin," *J. Am. Chem. Soc.*, 86:304–305 (1964); and Stewart, J. M., and Young, J. D., *Solid Phase Peptide Synthesis.* 2 $^{nd}$ ed., Pierce Chemical Co., Rockford, Ill. (1964) on an automated synthesizer (Advanced ChemTech 440MOS, Louisville, Ky.). The amino acids Boc-Tyr(2ClBzl), Boc-diaminopropionic acid [Dpr(Fmoc)], Boc-Asp(OFm), Boc-Arg(Tos), Boc-Phe, Boc-His(Bom), Boc-DPhe, Boc-Trp(CHO), Boc-Asn, and Boc-Ala are commercially available. The peptides were assembled on commercially available pMBHA resin (0.28 meq/g substitution). All reagents were ACS grade or better.

The synthesis was performed using a commercially available 40 well Teflon reaction block with a course Teflon frit. Approximately 200 mg resin (0.08 mmole) was added to each reaction block well. With reaction volume limitations, each peptide can be synthesized in two separate reaction wells. The resin was allowed to swell for 2 hrs in 5 mL dimethylformamide (DMF) and deprotected using 4 mL 50% trifluroacetic acid (TFA), 2% anisole in dichloromethane (DCM) for 3 min followed by a 20 min incubation at 500 rpms and washed with DCM (4.5 mL, 2 min, 500 rpms 3 times). The peptide-resin salt was neutralized by the addition of 4 mL 10% diisopropylethylamine (DIEA) in DCM (3 min, 500 rpms, 2 times) followed by a DCM wash (4.5 mL, 2 min, 500 rpms 4 times). Free amino acid groups were identified on the resin using a Kaiser test.

The growing peptide chain was added to the amide-resin using the general amino acid cycle as follows: 500 μL DMF is added to each reaction well to "wet the frit," 3-fold excess amino acid starling from the C-terminus is added [400 μL of 0.5M solution in 0.5M N-hydroxybenzotriazole (HOBt) in DMF] followed by the addition of 400 μL 0.5M N,N'-diisopropylcarbodiimide (DIC) in DMF and the reaction well volume is brought up to 3 mL using DMF. The coupling reaction is mixed for 1 hr at 500 rpms, followed by emptying of the reaction block by positive nitrogen gas pressure. A second coupling reaction is performed by the addition of 500 μL DMF to each reaction vessel, followed by the addition of 400 μL of the respective amino acid (3-fold excess), 400 μL 0.5M O-benzotriazolyl-N,N,N',N'-tetramethyluronium hexafluorophosphate (HBTU), 300 μL 1 M DIEA, the reaction well volume is brought up to 3 mL, with DMF, and mixed at 500 rpm for 1 hr. After the second coupling cycle, the reaction block is emptied and the resin-Nα-protected peptide is washed with DCM (4.5 mL 4 times). Nα-Boc deprotection is performed by the addition of 4 mL 50% TFA, 2% anisole in DCM and mixed for 5 min at 500 rpms followed by a 20 min deprotection at 500 rpm. The reaction well is washed with 4.5 mL DCM (4 times), neutralized with 10% DIEA (3 min, 500 rpms, 2 times) followed by a DCM wash (4.5 mL, 2 min, 500 rpms 4 times), and the next coupling cycle is performed as described above.

The Fmoc and OFm protecting groups are removed from Dpr and Asp, respectively by treatment with 4.5 mL 25% piperidine in DMF (20 min at 500 rpm) with a positive Kaiser test results. The lactam bridge between the Asp and Dpr amino acids is formed using 5-fold excess benzotriazole-2-yloxy-tris-(dimethylamino) phosphonium hexafluorophosphate (BOP) and 6-fold excess DIEA as coupling agents and mixing at 500 rpms. The lactam bridges were formed (negative Kaiser test) after approximately 3 days at room temperature. Deprotection of the remaining amino acid side chains and cleavage of the amide-peptide from the resin was performed by incubation the peptide-resin with anhydrous hydrogen fluoride (HF, 5 mL, 0° C., 1 hr) and 5% m-cresol, 5% thioanisole as scavengers.

After the reaction is complete and the HF has been distilled off, the peptide is ether precipitated (50 mL×1) and washed with 50 mL cold (4°) anhydrous ethyl ether. The peptide is filtered off using a course frit glass filter and dissolved in glacial acetic acid, frozen and lyophilized. The crude peptide yields ranged from 60% to 90% of the theoretical yields. A 40 mg sample of crude peptide was purified by RP-HPLC using a Shimadzu chromatography system with a photodiode array detector and a semi-preparative reversed phase high performance liquid chromatography (RP-HPLC) $C_{18}$ bonded silica column (Vydac 218TP1010, 1.0×25 cm) and lyophilized. The purified peptide was >95% pure as determined by analytical RP-HPLC and had the correct molecular mass.

EXAMPLE 3—ASSAYS

For cell culture and transfection, HEK-293 cells were maintained in Dulbecco's modified Eagle's medium (DMEM) with 10% fetal calf serum and seeded 1 day prior to transfection at 1 to 2×10⁶ cell/100-mm dish. Melanocortin receptor DNA in the $pCDNA_3$ expression vector (20 μg) were transfected using the calcium phosphate method. Stable receptor populations were generated using G418 selection (1 mg/mL) for subsequent bioassay analysis.

Functional Bioassay

In the functional bioassay studies, HEK-293 cells stably expressing the mouse MC1, MC3, MC4 and MC5 receptors were transfected with 4 μg CRE/β-galactosidase reporter gene as previously described in Haskell-Luevano, C. et al., "Characterization of melanocortin NDP-MSH agonist peptide fragments at the mouse central and peripheral melanocortin receptors," *J. Med. Chem.*, 44:2247–2252 (2001); Haskell-Luevano, C. et al., "Structure activity studies of the melanocortin-4 receptor by in vitro mutagenesis: identification of agouti-related protein (AGRP), melanocortin agonist and synthetic peptide antagonist interaction determinants," *Biochemistry*, 40:6164–6179 (2001); and Chen, W. et al., "A colorimetric assay for measuring activation of Gs- and Gq-coupled signaling pathways," *Anal. Biochem.*, 226:349–354 (1995)). 5,000 to 15,000 post transfection cells were plated into 96 well Primera plates (Falcon) and incubated overnight. Forty-eight hours post-transfection the cells were stimulated with 100 μL peptide ($10^{-4}$–$10^{-12}$ M) or forskolin ($10^{-4}$ M) control in assay medium (DMEM containing 0.1 mg/mL BSA and 0.1 mM isobutylmethylxanthine) for 6 hrs. The assay media was aspirated and 50 μL of lysis buffer (250 mM Tris-HCl pH=8.0 and 0.1% Triton X-100) was added. The plates were stored at −80° overnight.

The plates containing the cell lysates were thawed the following day. Aliquots of 10 μL were taken from each well and transferred to another 96-well plate for relative protein determination. To the cell lysate plates, 40 μL phosphate-buffered saline with 0.5% BSA was added to each well. Subsequently, 150 μL substrate buffer (60 mM sodium phosphate, 1 mM $MgCl_2$, 10 mM KCl, 5 mM β-mercaptoethanol, 200 mg/100 mL ONPG) was added to each well and the plates were incubated at 37°.

The sample absorbance, $OD_{405}$, was measured using a 96 well plate reader (Molecular Devices). The relative protein was determined by adding 200 μL 1:5 dilution Bio Rad G250 protein dye:water to the 10 μL cell lysate sample taken previously, and the $OD_{595}$ was measured on a 96 well plate reader (Molecular Devices). Data points were normalized both to the relative protein content and non-receptor dependent forskolin stimulation. The antagonistic properties of these compounds were evaluated by the ability of these ligands to competitively displace the MTII agonist (Bachem) in a dose-dependent manner, at up to 10 μM concentrations. The $pA_2$ values were generated using the Schild analysis method described in Schild, H. O., "pA, A New Scale for the Measurement of Drug Antagonism," *Brit. J. Pharmacol.*, 2:189–206 (1947).

Binding Assays

In the binding assays, $^{125}$I-NDP-MSH was prepared using a modified chloramine-T method as previously described by Yang, et al., "Characterization of Agouti-related protein binding to melanocortin receptors," *Mol. Endo.*, 13:148–155 (1999). Using 50 mM sodium phosphate buffer pH 7.4 as the reaction buffer, $^{125}$I-Na (0.5 mCi, Amersham Life Sciences, Inc., Arlington Heights, Ill.) was added to 20 mg of NDP-MSH (Bachem, Torrance, Calif.) in 5 mL buffer. To initiate the reaction, 10 mL of a 2.4 mg/ml solution of chloramine T (Sigma Chemical Co., St. Louis, Mo.) was added for 15 seconds with gentle agitation. This reaction was terminated by the addition of 50 mL of a 4.8 mg/ml solution of sodium metabisulfite (Sigma Chemical Co.) for 20 seconds with gentle agitation.

The reaction mixture was then diluted with 200 mL 10% bovine serum albumin and the resultant mixture layered on a Bio-Gel P2 (Bio-Rad Labs, Hercules, Calif.) column (1.0×30 cm Econocolumn, Bio-Rad Labs) for separation by size exclusion chromatography using 50 mM sodium phosphate buffer, pH 7.4 as column eluant. Fifteen drop fractions (ca 500 mL) were collected into glass tubes containing 500 mL of 1% BSA. Each fraction was then counted on the Apex Automatic Gamma Counter (ICN Micromedic Systems Model 28023, Huntsville, Ala. with RIA AID software, Robert Maciel Associates, Inc., Arlington, Mass.) to determine peak $^{125}$I incorporation fractions.

Receptor Binding Studies

One day preceding the experiment, 0.1–0.3×10$^6$ cells/well of HEK-293 cells (prepared and maintained as described above) were plated into Primera 24 well plates (Falcon). The peptides (10$^{-5}$ M) and NDP-MSH (10$^{-6}$ to 10$^{-12}$ M) were used to competitively displace the $^{125}$I-radiolabeled NDP-MSH (100,000 cpm/well). Dose-response curves (10$^{-6}$ to 10$^{-12}$ M) of NDP-MSH and IC$_{50}$ values were generated and analyzed by nonlinear least squares analysis (see Bowen, W. P., and Jerman, J. C., "Nonlinear regression using spreadsheets," *TiPS*, 16:413–417 (1995)) and the PRISM program (v3.0, GraphPad Inc.). The peptides that did not possess agonist or antagonist pharmacology in the functional assay were examined for their ability to competitively displace $^{125}$I-NDP-MSH (100,000 cpm/well) at 10$^{-5}$ M concentrations. The percent total specific binding was determined based upon the non-specific values obtained using 10$^{-6}$ M NDP-MSH and the NDP-MSH dose response curves as controls. The standard deviation errors are derived from the average percent specific binding values from three independent experiments and using the PRISM program (v3.0, GraphPad Inc.).

Data Analysis

For data analysis, EC$_{50}$ and pA$_2$ values represent the mean of duplicate experiments performed in triplet, quadruplet or more independent experiments. EC$_{50}$ and pA$_2$ estimates, and their associated standard errors, were determined by fitting the data to a nonlinear least-squares analysis using the PRISM program (v3.0, GraphPad Inc.).

The peptides of the subject invention (i.e., SEQ ID NOS: 3–7, 9–10, 12–18, and 20–43) were synthesized using standard procedures and purified to homogeneity using semi-preparative reversed-phased high pressure liquid chromatography as provided above in Examples 1 and 2. Table 1 summarizes the agonist EC$_{50}$ values and antagonist pA$_2$ values of peptides of the present invention at the mouse melanocortin receptors, mMC1R, mMC3R, mMC4R, and mMC5R. The errors indicated in Table 1 represent the standard error of the mean determined from at least three independent experiments. The antagonist pA$_2$ values were determined using the Schild analysis and the agonist MTII. The value ">100,000" indicates that the compound was examined but lacked agonist or antagonist properties at up to 100 μM concentrations. Slight agonist denotes that some stimulatory response was observed at 100 μM concentrations, but not enough to determine an EC$_{50}$ value.

TABLE 1

Pharmacological results of chimeric peptides of the present invention at the mouse melanocortin receptors

| | EC$_{50}$ (nM) | | | |
|---|---|---|---|---|
| Compound | mMC1R) | mMC3R | mMC4R | mMC5R |
| hAGRP (109–118) | 5,120 ± 3,040 | >100,000 | pA$_2$ = 6.8 ± 0.24 | >100,000 |
| α-MSH | 0.55 ± 0.09 | 0.79 ± 0.14 | 5.37 ± 0.62 | 0.44 ± 0.09 |
| NDP-MSH | 0.038 ± 0.012 | 0.098 ± 0.013 | 0.21 ± 0.03 | 0.071 ± 0.012 |
| MTII | 0.020 ± 0.003 | 0.16 ± 0.03 | 0.087 ± 0.008 | 0.16 ± 0.03 |
| SEQ ID NO: 1 | 61.3 ± 17.9 | Slight Agonist >100,000 | Partial agonist pA$_2$ = 6.1 ± 0.2 | 238.7 ± 100 |
| SEQ ID NO: 2 | >100,000 | >100,000 | >100,000 | >100,000 |
| SEQ ID NO: 3 | 1,730 ± 310 | pA$_2$ = 5.7 ± 0.2 | pA$_2$ = 5.9 ± 0.2 | >100,000 |
| SEQ ID NO: 4 | 13,500 ± 3,100 | >100,000 | Partial agonist 15,900 ± 7,300 | >100,000 |
| SEQ ID NO: 5 | 6,120 ± 2,300 | Slight Agonist | 10,900 ± 2,900 | 2,220 ± 1,100 |
| SEQ ID NO: 6 | 19,700 ± 4,300 | Slight agonist | 13,400 ± 400 | 3,900 ± 1,800 |
| SEQ ID NO: 7 | 4,850 ± 1,450 | Slight agonist | 450 ± 160 | 124 ± 25 |
| SEQ ID NO: 8 | 13,300 ± 1,700 | Slight agonist | >100,000 | 100,000 |
| SEQ ID NO: 9 | 59.5 ± 16.7 | 309 ± 120 | 57.1 ± 4.4 | 90.0 ± 22.0 |
| SEQ ID NO: 10 | 0.21 ± 0.09 | 0.99 ± 0.34 | 0.18 ± 0.04 | 0.55 ± 0.14 |
| SEQ ID NO: 11 | 1,960 ± 500 | pA$_2$ = 6.2 ± 0.3 | pA$_2$ = 6.2 ± 0.1 | >100,000 |
| SEQ ID NO: 12 | >100,000 | >100,000 | >100,000 | >100,000 |
| SEQ ID NO: 13 | Partial agonist 19,900 ± 5,100 | >100,000 | >100,000 | >100,000 |
| SEQ ID NO: 14 | Partial agonist 7,220 ± 2,200 | Partial agonist 20,500 ± 6,800 | >100,000 | Partial agonist 24,400 ± 6,700 |
| SEQ ID NO: 15 | 59.9 ± 8.1 | 480 ± 49 | 930 ± 120 | 327 ± 118 |
| SEQ ID NO: 16 | Slight agonist | >100,000 | >100,000 | Slight agonist |
| SEQ ID NO: 17 | 7.28 ± 0.76 | 6,210 ± 990 | Slight agonist | 450 ± 110 |
| SEQ ID NO: 18 | 3,630 ± 320 | >100,000 | >100,000 | Slight agonist |
| SEQ ID NO: 19 | >100,000 | >100,000 | >100,000 | >100,000 |
| SEQ ID NO: 20 | Partial agonist 38,300 ± 8,700 | >100,000 | >100,000 | >100,000 |
| SEQ ID NO: 21 | >100,000 | >100,000 | >100,000 | >100,000 |
| SEQ ID NO: 22 | 440 ± 49 | 14,400 ± 3,700 | 5,000 ± 900 | 3,600 ± 200 |
| SEQ ID NO: 23 | 2,630 ± 830 | Slight agonist | >100,000 | Slight agonist |
| SEQ ID NO: 24 | 7.20 ± 2.89 | 29.0 ± 7.5 | 0.36 ± 0.07 | 0.46 ± 0.18 |
| SEQ ID NO: 25 | 14000 ± 1700 | Partial agonist 30300 ± 1400 | 14700 ± 1000 | 690 ± 98 |
| SEQ ID NO: 26 | 66.5 ± 26.8 | 23800 ± 18900 | 32.5 ± 16.7 | 2.06 ± 0.67 |
| SEQ ID NO: 27 | 350 ± 160 | 13500 ± 3700 | 710 ± 170 | 50.1 ± 9.6 |
| SEQ ID NO: 28 | 22.1 ± 18 | Partial agonist pA$_2$ = 7.2 ± 0.2 | 0.63 ± 0.20 | 7.16 ± 0.22 |

TABLE 1-continued

Pharmacological results of chimeric peptides of the present invention at the mouse melanocortin receptors

| | EC$_{50}$ (nM) | | | |
|---|---|---|---|---|
| Compound | mMC1R) | mMC3R | mMC4R | mMC5R |
| SEQ ID NO: 29 | 6.04 ± 1.36 | Partial agonist pA$_2$ = 7.2 ± 0.6 | 0.64 ± 0.17 | 3.15 ± 1.38 |
| SEQ ID NO: 30 | 690 ± 150 | pA$_2$ = 6.4 ± 0.2 | 115 ± 26 | 440 ± 230 |
| SEQ ID NO: 31 | 10300 ± 3200 | 13200 ± 3400 | 16700 ± 1300 | 7900 ± 4000 |
| SEQ ID NO: 32 | 0.30 ± 0.05 | pA$_2$ = 8.9 ± 0.1 | Partial agonist pA$_2$ = 9.4 ± 0.4 | 2.33 ± 0.96 |
| SEQ ID NO: 33 | 5.56 ± 3.40 | pA$_2$ = 8.3 ± 0.2 | Partial agonist pA$_2$ = 9.3 ± 0.1 | 22.3 ± 10.6 |
| SEQ ID NO: 34 | 9.20 ± 0.97 | 320 ± 250 | 0.57 ± 0.08 | 3.13 ± 1.89 |
| SEQ ID NO: 35 | 3.87 ± 0.85 | 33.0 ± 21.3 | 0.57 ± 0.07 | 5.27 ± 2.12 |
| SEQ ID NO: 36 | 990 ± 290 | 17300 ± 290 | 4300 ± 1900 | 3200 ± 2400 |
| SEQ ID NO: 37 | 680 ± 82 | 30800 ± 4200 | 8600 ± 2200 | 800 ± 120 |
| SEQ ID NO: 38 | 1000 ± 170 | 39200 ± 13200 | 7200 ± 1800 | 700 ± 110 |
| SEQ ID NO: 39 | 0.53 ± 0.13 | 5.56 ± 2.72 | 0.27 ± 0.12 | 1.93 ± 1.10 |
| SEQ ID NO: 40 | 0.20 ± 0.05 | 6.50 ± 1.87 | 0.67 ± 0.25 | 0.95 ± 0.40 |
| SEQ ID NO: 41 | 11.6 ± 3.5 | 450 ± 130 | 42.6 ± 9.7 | 3.43 ± 0.90 |
| SEQ ID NO: 42 | 21.6 ± 10.3 | 3400 ± 1200 | 260 ± 99 | 42.7 ± 10.0 |
| SEQ ID NO: 43 | 2.61 ± 0.14 | 14.0 ± 1.8 | 0.66 ± 0.20 | 4.87 ± 2.29 |

EXAMPLE 4—AGRP/MCR AGONIST PEPTIDES

In accordance with the present invention, the hAGRP (109–118) decapeptide template was utilized to systematically replace the hAGRP(111–113) Arg-Phe-Phe antagonist amino acids with melanocortin agonist Phe-Arg-Trp residues (Table 1). For the peptide represented by SEQ ID NO:1, the Phe113 of the hAGRP(109–118) decapeptide template containing a disulfide bridge was inverted to the D-amino acid. SEQ ID NOS:2–11 replaced the disulfide bridge with a side chain lactam bridge (Asp-Dpr) to determine if the lactam bridge would result in pharmacological differences while maintaining a similar ring size as the disulfide bridge.

SEQ ID NO:2 was synthesized as a control, replacing the Arg-Phe-Phe hAGRP antagonist amino acids with Ala-Ala-Ala. The peptide of SEQ ID NO:2 lacked agonist or antagonist activity at the melanocortin receptors at up to 100 μM concentrations, and was unable to competitively displace radiolabeled $^{125}$I-NDP-MSH beyond a ligand 25% binding at 10 μM concentrations.

SEQ ID NO:3 contains the lactam bridge instead of the disulfide bridge. Comparison of the hAGRP(109–118) to SEQ ID NO:3 resulted in nearly equipotent pharmacology, within experimental error at the mMC1R, except at the mMC4R where the lactam bridge resulted in a 8-fold decrease in antagonist potency and μM antagonist pharmacology was detectable at the mMC3R.

Both the Phe-Arg-Trp and the Trp-Arg-Phe sequences were substituted into the hAGRP(109–118) decapeptide. Comparison of SEQ ID NOS:4 and 6, both of which contain the L-Phe configuration, resulted in μM mMC1R agonist activity while SEQ ID NO:4 lacked full agonist activity or antagonist activity at the mMC3–5Rs, and SEQ ID NO:6 resulted in μM full agonist activity at the mMC4R and mMC5R, while only possessing slight agonist activity at the mMC3R.

Previous studies of the agonist melanocortin peptides identified that inversion of chirality of Phe$^7$ to DPhe$^7$ of α-MSH resulted in 10-to 1000-fold increased potency. Accordingly, in SEQ ID NO:5, Trp-Arg-DPhe amino acids were substituted at the hAGRP 111–113 positions and in SEQ ID NO:7, DPhe-Arg-Trp residues were substituted at the AGRP Arg-Phe-Phe (111–113) positions to evaluate any increase in agonist activity. Consistent with previous observations for the melanocortin-based agonists, SEQ ID NOS: 5 and 7 containing the D-Phe configuration generally resulted in increased agonist potency, as compared with the corresponding L diastereoisomeric peptide, except at the mMC3R where only slight agonist activity was observed at up to 100 μM concentrations.

Truncation studies of the melanocortin agonist peptides using α-MSH and NDP-MSH templates resulted in the observation that inclusion of the His$^6$ amino acid (α-MSH numbering) resulted in significant increased agonist potency at the melanocortin receptors. To examine the effect on enhancing agonist ligand potency of the hAGRP(109–118) template, the His$^6$ amino acid of the melanocortin agonist putative message sequence (His-Phe-Arg-Trp) was inserted into the lactam modified hAGRP (109–118) decapeptide template to yield the peptide of SEQ ID NO:8. In comparing SEQ ID NOS:8 and 3, insertion of the His residue into the AGRP(109–118) template resulted in a 8-fold decreased mMC1R agonist potency, but antagonist activity was absent at the mMC3 and mMC4 receptors and SEQ ID NO:8 bound to these receptors (mMC3R and mMC4R) at less than 50% specific binding.

Substitution of the His residue (His-Phe-Arg-Trp) for the His-Arg-Phe-Phe motif of SEQ ID NO:8 resulted in the generation of the peptide represented by SEQ ID NO:9. SEQ ID NO:9 possesses nM full agonist potency at all the examined melanocortin receptors.

SEQ ID NO:10, which contains the agonist His-DPhe-Arg-Trp sequence in the AGRP antagonist template, resulted in sub nM agonist potency at the mMC1R and mMC3–5Rs, within experimental error of α-MSH at these receptors, with the exception that at the mMC4R, SEQ ID NO:10 was ca 30-fold more potent than α-MSH.

The N-terminal Ac-Ser-Tyr-Ser-Nle and C-terminal Lys-Pro-Val-NH$_2$ amino acids of the melanocortin agonist NDP-MSH were substituted at the respective peptide termini of the lactam bridge hAGRP (109–118) decapeptide to yield the peptide of SEQ ID NO:11. SEQ ID NO:11 resulted in nearly equipotent melanocortin receptor pharmacology as SEQ ID NO:3 that lacked the N- and C-terminal agonist amino acid extension, supporting the hypothesis that the central "core" residue 109–118 region of the hAGRP antagonist determines melanocortin receptor potency and pharmacology.

In accordance with the present invention, natural and/or unnatural amino acids were substituted within the melanocortin agonist Phe-Arg-Trp residues utilized to replace the hAGRP(111–113) Arg-Phe-Phe amino acids to yield the peptides of SEQ ID NOS:24–43. SEQ ID NOS:28–30 resulted in antagonist activity at mMC3R and agonist activity at mMC4 and mMC5 receptors.

EXAMPLE 5—NDP-MSH/AGRP PEPTIDES

In accordance with the present invention, the linear tridecapeptide NDP-MSH agonist template was used as a base in which DPhe-Arg-Trp amino acids were replaced with the hAGRP(111–113) Arg-Phe-Phe residues. The peptide of SEQ ID NO:12 was synthesized as a control peptide having the agonist DPhe-Arg-Trp residues replaced with Ala-Ala-Ala. SEQ ID NO:12 resulted in a complete loss of agonist activity at up to 100 μM concentrations and was unable to bind to the MC3R or MC4R more than 25%. Thus, the bioactivity of the control peptide of SEQ ID NO:12 verifies the importance of the DPhe-Arg-Trp residues for melanocortin receptor activity.

The peptide of SEQ ID NO:13 has the NDP-MSH linear tridecapeptide template substituted with hAGRP residues in the Phe-Phe-Arg orientation and deletion of the His$^6$ residue (α-MSH numbering). SEQ ID NO:13 resulted in a lack of agonist or antagonist activity at up to 100 μM at the MC3–5 receptors, but was a partial agonist at the MC1R.

In contrast, the peptide of SEQ ID NO:14 contains the HIS$^6$ amino acid and the AGRP residues in the Phe-Phe-Arg orientation. SEQ ID NO:14 resulted in partial agonist activities and no antagonist activity at the MC1R, MC3R, and MC5R with little observable binding or activity at the MC4R.

Incorporation of the hAGRP(111–113) residues into the NDP-MSH template in the Arg-Phe-Phe, resulted in the peptide of SEQ ID NO:15. Peptides of SEQ ID NO:15 have nM melanocortin receptor agonist potency.

These results, and those presented above for the hAGRP (109–118) template, demonstrate that the hAGRP(111–113) Arg-Phe-Phe antagonist residues mimic the agonist Phe-Arg-Trp amino acids in a similar topographical orientation as the linear sequences. As discussed previously, it has been well documented that inversion of chirality of the melanocortin agonist Phe$^7$ (α-MSH numbering) to the D configuration resulted in ligands possessing enhanced melanocortin receptor potency.

To correlate which hAGRP(112–113) Phe residue corresponds to the melanocortin agonist Phe$^7$ amino acid in regards to putative ligand-receptor interactions, systematic stereochemical inversion of the hAGRP(111–113) Arg-Phe-Phe residues in the peptide of SEQ ID NO:15 resulted in SEQ ID NOS:16–18. Generally, for SEQ ID NOS:16–18, stereochemical inversion of the Arg-Phe-Phe residues in the NDP-MSH template resulted in dramatic decreases in melanocortin receptor activity, with the exception of SEQ ID NO:17, as compared with SEQ ID NO:15.

SEQ ID NO:17 (NDP-MSH linear template) containing the DPhe that putatively corresponds to the hAGRP Phe$^{112}$ residue, resulted in only an 8-fold increase in mMC1R agonist potency, a 13-fold decreased mMC3R agonist potency, conversion from a full mMC4R agonist to only a slight agonist at 100 μM concentrations and equipotent mMC5R agonist potency, compared with SEQ ID NO:15.

EXAMPLE 6—MTII/AGRP PEPTIDES

In accordance with the present invention, the cyclic heptapeptides MTII agonist template was used as a base in which DPhe-Arg-Trp amino acids were replaced with the hAGRP(111–113) Arg-Phe-Phe residues to synthesize the peptides of SEQ ID NOS:20–23. The peptide of SEQ ID NO:19 was synthesized with the MTII DPhe-Arg-Trp residues substituted with Ala-Ala-Ala as a control to the peptides of SEQ ID NOS:20–23.

With the peptide of SEQ ID NO:20, the DPhe-Arg-Trp amino acid sequence of cyclic MTII was substituted with the hAGRP(111–113) Arg-Phe-Phe residues. SEQ ID NO:20 resulted in a loss of full agonist activity at the MC3–5 receptors and only possessed μM partial agonist activity at the MC1R.

Stereochemical inversion of the hAGRP(111–113) Arg-Phe-Phe residues of SEQ ID NO:20 resulted in the peptide of SEQ ID NO:21, wherein DArg-Phe-Phe was incorporated into the MTII peptide template. The peptide of SEQ ID NO:21 lost the ability to generate a full agonist response at up to 100 μM concentrations at the melanocortin receptors.

However, SEQ ID NO:22 (MTII cyclic template) containing the DPhe that putatively corresponds to the hAGRP Phe$^{112}$ residue, resulted in converting the peptide with the corresponding L-Phe isomer (SEQ ID NO:20) from an mMC1R partial agonist into an nM full agonist, and a ligand possessing full μM agonist activity at the mMC3–5 receptors.

These results suggest that the antagonist hAGRP Phe$^{112}$ may be mimicking the melanocortin agonist DPhe$^7$ interactions with the receptor in the cyclic hAGRP(109–118) and MTII peptide templates, in terms of enhancing general melanocortin receptor agonist potency. Although this latter speculation remains to be experimentally verified, this is the first experimental evidence suggesting that the hAGRP Phe$^{112}$ antagonist residue may topographically correlate with the melanocortin agonist Phe$^7$ amino acid in terms of putative ligand-mMC4R interactions.

The peptide of SEQ ID NO:23 contains the Arg-Phe-DPhe motif substituted for the DPhe-Arg-Trp amino acids in the MTII peptide template. SEQ ID NO:23 demonstrated slight agonist activity at 100 μM at the MC3R and MC5R, but was a μM MC1R agonist.

EXAMPLE 7—MELANOCORTIN RECEPTOR SELECTIVE LIGANDS

The central MC3 and MC4 receptors expressed in the brain have been associated with the physiological role of weight and energy homeostasis through the use of knockout mice and in vivo feeding studies (see Fan, W. et al, "Role of melanocortinergic neurons in feeding and the agouti obesity syndrome," *Nature,* 385:165–168 (1997); Huszar, D. et al., "Targeted disruption of the melanocortin-4 receptor results in obesity in mice," *Cell,* 88:131–141 (1997); Butler, A. A. et al., "A unique metabolic syndrome causes obesity in the melanocortin-3 receptor-deficient mouse," *Endocrinology,* 141:3518–21 (2000); and Chen, A. S. et al., "Inactivation of the mouse melanocortin-3 receptor results in increased fat mass and reduced lean body mass," *Nat Genet,* 26:97–102 (2000)). Due to the neuroanatomical overlap in some regions of the brain of the MC3 and MC4 receptor mRNA and the complexity of energy homeostatic pathways, melanocortin ligands selective for either of these melanocortin receptor isoforms are desirable for in vivo studies.

In the subject invention, the peptide of SEQ ID NO:7 (Tyr-c[Asp-DPhe-Arg-Trp-Asn-Ala-Phe-Dpr]-Tyr-NH$_2$) resulted in a ligand that is only a slight mMC3R agonist (is not a mMC3R antagonist, does not bind at the mMC3R greater than 25% specific binding at 10 µM concentrations, but possess a 450 nM agonist EC$_{50}$ value at the mMC4R resulting in a >200-fold MC4R versus MC3R selective compound.

The peptide of SEQ ID NO:17 (Ac-Ser-Tyr-Ser-Nle-Glu-His-Arg-DPhe-Phe-Gly-Lys-Pro-Val-NH$_2$), resulted in a potent nM mMC1R agonist possessing high nM agonist activity at the mMC5R, µM agonist activity at the mMC3R and only slight agonist activity at the mMC4R (not an antagonist and does not bind to the mMC4R at greater than 25% specific binding at 10 µM concentrations. Thus, SEQ ID NO:17 is a 850-fold MC1R versus MC3R selective, >16-fold MC5R versus MC3R selective, and 62-fold MC1R versus MC5R selective peptide.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A peptide that is biologically active at melanocortin receptors comprising an AGRP(109–118) analogue template of SEQ ID No: 3 wherein AGRP (111–113) residues of the AGRP (109–118) template are substituted with a melanocortin agonist-based bioactive determinant sequence wherein
   a) the melanocortin agonist-based bioactive determinant sequence is selected from the group consisting of:
      i) Trp-Arg-Phe
      ii) Trp-Arg-DPhe
      iii) Phe-Arg-Trp
      iv) DPhe-Arg-Trp
      v) His-Phe-Arg-Trp; and
      vi) His-DPhe-Arg-Trp.

2. The peptide according to claim 1, wherein the peptide is of any SEQ ID Nos. 4–7, 9 and 10.

3. A peptide that is biologically active at melanocortin receptors comprising AGRP (109–118) analogue template of SEQ ID No: 3, wherein AGRP (111–113) residues of the AGRP(109–118) template are substituted with the sequence Xaa1-Xaa2-Xaa3-Xaa4 wherein Xaa1 is selected from His, Ala, Atc, Bip, Lys, Nal(1'), Nal(2'), (pI)Phe and Tic, or is absent;
Xaa2 is selected from Trp, Phe, DPhe, Ala, Ato, Bip, Lys, Nal(1'), Nal(2'), (pI)Phe and Tic,
Xaa3 is selected from Arg, Ala, Atc, Bip, Lys, Nal(1'), Nal(2'), (pI)Phe and Tic;
Xaa4 is selected from Phe, DPhe, Trp, Ala, Atc, Bip, Lys, Nal(1'), Nal(2'), (pI)Phe and Tic; and
wherein, at least one of Xaa1, Xaa2, Xaa3 or Xaa4 is selected from Ala, Atc, Bip, Lys, Nal(1'), Nal(2'), (pI)Phe and Tic.

4. A peptide that is biologically active at melanocortin receptors comprising a sequence selected from the group consisting of SEQ ID Nos: 2 and 24–43.

5. The peptide according to claim 1, wherein the peptide further comprises a lactam bridge that is substituted for the disulfide bridge of the AGRP (109-118) analogue template.

6. The peptide according to claim 5, wherein the peptide is SEQ ID No: 11.

7. The peptide according to claim 5, wherein the peptide further comprises a second and a third bioactive determinant sequences at the N-terminal and C-terminal, respectively, wherein the second bioactive determinant sequence at the N-terminal is Ser-Tyr-Ser-Nle (amino acid residues 2–5 of SEQ ID No: 11) and the third bioactive determinant sequence at the C-terminal is Lys-Pro-Val amino acid residues.

8. A pharmaceutical composition comprising a peptide that is biologically active at melanocortin receptors comprising an AGRP (109–118) analogue template of SEQ ID No: 3 wherein AGRP (111–113) residues of the AGRP (109–118) template are substituted with a melanocortin agonist-based bioactive determinant sequence wherein
a) the melanocortin agonist-based bioactive determinant sequence is selected from the group consisting of:
i) Trp-Arg-Phe
ii) Trp-Arg-DPhe
iii) Phe-Arg-Trp
iv) DPhe-Arg-Trp
v) His-Phe-Arg-Trp; and
vi) His-DPhe-Arg-Trp.

9. The pharmaceutical composition according to claim 8, wherein the peptide is of any SEQ ID Nos. 4–7, 9 and 10.

10. A pharmaceutical composition comprising a peptide that is biologically active at melanocortin receptors comprising an AGRP (109–118) analogue template of SEQ ID NO: 3, wherein AGRP (111–113) residues of the AGRP (109–118) template are substituted with the sequence Xaa1-Xaa2-Xaa3-Xaa4 wherein,
Xaa1 is selected from His, Ala, Atc, Bip, Lys, Nal(1'), Nal(2'), (pI)Phe and Tic, or is absent;
Xaa2 is selected from Trp, Phe, DPhe, , Ala, Atc, Bip, Lys, Nal(1'), Nal(2'), (pI)Phe and Tic,
Xaa3 is selected from Arg, Ala, Atc, Bip, Lys, Nal(1'), Nal(2'), (pI)Phe and Tic;
Xaa4 is selected from Phe, DPhe, Trp, Ala, Atc, Bip, Lys, Nal(1'), Nal(2'), (pI)Phe and Tic; and
wherein, at least one of Xaa1, Xaa2, Xaa3 or Xaa4 is selected from Ala, Atc, Bip, Lys, Nal(1'), Nal(2'), (pI)Phe and Tic.

11. A pharmaceutical composition comprising a peptide of claim 4.

12. The pharmaceutical composition according to claim 8, wherein the peptide further comprises a lactam bridge that is substituted for the disulfide bridge of the AGRP (109–118) analogue template.

13. The pharmaceutical composition according to claim 12, wherein the peptide is of SEQ ID No. 11.

14. The pharmaceutical composition according to claim 12, wherein the peptide further comprises a second and a third bioactive determinant sequences at the N-terminal and C-terminal, respectively, wherein the second bioactive determinant sequence at the N-terminal is Ser-Tyr-Ser-Nle (amino acid residues 2–5 of SEQ ID No: 11) and the third bioactive determinant sequence at the C-terminal is Lys-Pro-Val amino acid residues.

15. The composition of claim 8, wherein the composition is an oral composition.

* * * * *

UNITED STATES PATENT AND TRADEMARK OFFICE
CERTIFICATE OF CORRECTION

PATENT NO. : 7,084,111 B2
APPLICATION NO. : 10/602394
DATED : August 1, 2006
INVENTOR(S) : Carrie Haskell-Luevano Page 1 of 1

It is certified that error appears in the above-identified patent and that said Letters Patent is hereby corrected as shown below:

Column 13,
Lines 24-25, "benzotriazole-2-yloxy-tris-(dimethylamino)"
should read --benzotriazole-1-yloxy-tris-(dimethylamino)--.

Column 49,
Line 3, "Xaa2 is selected from Trp, Phe, DPhe, Ala, Ato, Bip, Lys,"
should read --Xaa2 is selected from Trp, Phe, DPhe, Ala, Atc, Bip, Lys,--.

Column 50,
Line 13, "Xaa2 is selected from Trp, Phe, DPhe, , Ala, Atc, Bip, Lys,"
should read --Xaa2 is selected from Trp, Phe, DPhe, Ala, Atc, Bip, Lys,--.

Signed and Sealed this

Twelfth Day of December, 2006

JON W. DUDAS
*Director of the United States Patent and Trademark Office*

SEQUENCE LISTING

```
<160> NUMBER OF SEQ ID NOS: 43

<210> SEQ ID NO 1
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (5)..(5)
<223> OTHER INFORMATION: Xaa = DPhe

<400> SEQUENCE: 1

Tyr Cys Arg Phe Xaa Asn Ala Phe Cys Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (9)..(9)
<223> OTHER INFORMATION: Xaa = diaminoproprionic acid (Dpr)

<400> SEQUENCE: 2

Tyr Asp Ala Ala Ala Asn Ala Phe Xaa Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
```

```
<221> NAME/KEY: MISC_FEATURE
<222> LOCATION: (9)..(9)
<223> OTHER INFORMATION: Xaa = diaminoproprionic acid (Dpr)

<400> SEQUENCE: 3

Tyr Asp Arg Phe Phe Asn Ala Phe Xaa Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (9)..(9)
<223> OTHER INFORMATION: Xaa = diaminoproprionic acid (Dpr)

<400> SEQUENCE: 4

Tyr Asp Trp Arg Phe Asn Ala Phe Xaa Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (5)..(5)
<223> OTHER INFORMATION: Xaa = DPhe
<220> FEATURE:
<221> NAME/KEY: MISC_FEATURE
<222> LOCATION: (9)..(9)
<223> OTHER INFORMATION: Xaa = diaminoproprionic acid (Dpr)

<400> SEQUENCE: 5

Tyr Asp Trp Arg Xaa Asn Ala Phe Xaa Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (9)..(9)
<223> OTHER INFORMATION: Xaa = diaminoproprionic acid (Dpr)

<400> SEQUENCE: 6

Tyr Asp Phe Arg Trp Asn Ala Phe Xaa Tyr
1               5                   10

<210> SEQ ID NO 7
<211> LENGTH: 10
```

```
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(9)
<223> OTHER INFORMATION: Cyclization of this peptide
<220> FEATURE:
<221> NAME/KEY: MISC_FEATURE
<222> LOCATION: (3)..(3)
<223> OTHER INFORMATION: Xaa = DPhe
<220> FEATURE:
<221> NAME/KEY: MISC_FEATURE
<222> LOCATION: (9)..(9)
<223> OTHER INFORMATION: Xaa = diaminoproprionic acid (Dpr)

<400> SEQUENCE: 7

Tyr Asp Xaa Arg Trp Asn Ala Phe Xaa Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 8

Tyr Asp His Arg Phe Phe Asn Ala Phe Xaa Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 9

Tyr Asp His Phe Arg Trp Asn Ala Phe Xaa Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
```

```
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 10

Tyr Asp His Xaa Arg Trp Asn Ala Phe Xaa Tyr
1               5                   10

<210> SEQ ID NO 11
<211> LENGTH: 18
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)
<220> FEATURE:
<221> NAME/KEY: MISC_FEATURE
<222> LOCATION: (7)..(13)
<223> OTHER INFORMATION: Cyclization of this peptide
<220> FEATURE:
<221> NAME/KEY: MISC_FEATURE
<222> LOCATION: (14)..(14)
<223> OTHER INFORMATION: Xaa = diaminoproprionic acid (Dpr)

<400> SEQUENCE: 11

Xaa Ser Tyr Ser Xaa Tyr Asp Arg Phe Phe Asn Ala Phe Xaa Tyr Lys
1               5                   10                  15

Pro Val

<210> SEQ ID NO 12
<211> LENGTH: 14
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)

<400> SEQUENCE: 12

Xaa Ser Tyr Ser Xaa Glu His Ala Ala Ala Gly Lys Pro Val
1               5                   10

<210> SEQ ID NO 13
<211> LENGTH: 13
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)

<400> SEQUENCE: 13
```

Xaa Ser Tyr Ser Xaa Glu Phe Phe Arg Gly Lys Pro Val
1               5                   10

<210> SEQ ID NO 14
<211> LENGTH: 14
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)

<400> SEQUENCE: 14

Xaa Ser Tyr Ser Xaa Glu His Phe Phe Arg Gly Lys Pro Val
1               5                   10

<210> SEQ ID NO 15
<211> LENGTH: 14
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)

<400> SEQUENCE: 15

Xaa Ser Tyr Ser Xaa Glu His Arg Phe Phe Gly Lys Pro Val
1               5                   10

<210> SEQ ID NO 16
<211> LENGTH: 14
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)
<220> FEATURE:
<221> NAME/KEY: MISC_FEATURE
<222> LOCATION: (8)..(8)
<223> OTHER INFORMATION: Xaa = DArg

<400> SEQUENCE: 16

Xaa Ser Tyr Ser Xaa Glu His Xaa Phe Phe Gly Lys Pro Val
1               5                   10

<210> SEQ ID NO 17
<211> LENGTH: 14
<212> TYPE: PRT
<213> ORGANISM: Artificial Sequence
<220> FEATURE:
<223> OTHER INFORMATION: chimeric peptide
<220> FEATURE:

```
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)
<220> FEATURE:
<221> NAME/KEY: MISC_FEATURE
<222> LOCATION: (9)..(9)
<223> OTHER INFORMATION: Xaa = DPhe

<400> SEQUENCE: 17

Xaa Ser Tyr Ser Xaa Glu His Arg Xaa Phe Gly Lys Pro Val
1               5                   10

<210> SEQ ID NO 18
<211> LENGTH: 14
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (5)..(5)
<223> OTHER INFORMATION: Xaa = norleucine (Nle)
<220> FEATURE:
<221> NAME/KEY: MISC_FEATURE
<222> LOCATION: (10)..(10)
<223> OTHER INFORMATION: Xaa = DPhe

<400> SEQUENCE: 18

Xaa Ser Tyr Ser Xaa Glu His Arg Phe Xaa Gly Lys Pro Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (2)..(2)
<223> OTHER INFORMATION: Xaa = norleucine (Nle)
<220> FEATURE:
<221> NAME/KEY: MISC_FEATURE
<222> LOCATION: (3)..(8)
<223> OTHER INFORMATION: Cyclization of this peptide

<400> SEQUENCE: 19

Xaa Xaa Asp His Ala Ala Ala Lys
1               5

<210> SEQ ID NO 20
<211> LENGTH: 8
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
```

```
<221> NAME/KEY: MISC_FEATURE
<222> LOCATION: (2)..(2)
<223> OTHER INFORMATION: Xaa = norleucine (Nle)
<220> FEATURE:
<221> NAME/KEY: MISC_FEATURE
<222> LOCATION: (3)..(8)
<223> OTHER INFORMATION: Cyclization of this peptide

<400> SEQUENCE: 20

Xaa Xaa Asp His Arg Phe Phe Lys
1               5

<210> SEQ ID NO 21
<211> LENGTH: 8
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (2)..(2)
<223> OTHER INFORMATION: Xaa = norleucine (Nle)
<220> FEATURE:
<221> NAME/KEY: MISC_FEATURE
<222> LOCATION: (3)..(8)
<223> OTHER INFORMATION: Cyclization of this peptide
<220> FEATURE:
<221> NAME/KEY: MISC_FEATURE
<222> LOCATION: (5)..(5)
<223> OTHER INFORMATION: Xaa = DArg

<400> SEQUENCE: 21

Xaa Xaa Asp His Xaa Phe Phe Lys
1               5

<210> SEQ ID NO 22
<211> LENGTH: 8
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (2)..(2)
<223> OTHER INFORMATION: Xaa = norleucine (Nle)
<220> FEATURE:
<221> NAME/KEY: MISC_FEATURE
<222> LOCATION: (3)..(8)
<223> OTHER INFORMATION: Cyclization of this peptide
<220> FEATURE:
<221> NAME/KEY: MISC_FEATURE
<222> LOCATION: (6)..(6)
<223> OTHER INFORMATION: Xaa = DPhe

<400> SEQUENCE: 22

Xaa Xaa Asp His Arg Xaa Phe Lys
1               5

<210> SEQ ID NO 23
<211> LENGTH: 8
<212> TYPE: PRT
<213> ORGANISM: Artificial Sequence
<220> FEATURE:
<223> OTHER INFORMATION: chimeric peptide
<220> FEATURE:
```

-continued

```
<221> NAME/KEY: MISC_FEATURE
<222> LOCATION: (1)..(1)
<223> OTHER INFORMATION: Xaa = acetyl (Ac)
<220> FEATURE:
<221> NAME/KEY: MISC_FEATURE
<222> LOCATION: (2)..(2)
<223> OTHER INFORMATION: Xaa = norleucine (Nle)
<220> FEATURE:
<221> NAME/KEY: MISC_FEATURE
<222> LOCATION: (3)..(8)
<223> OTHER INFORMATION: Cyclization of this peptide
<220> FEATURE:
<221> NAME/KEY: MISC_FEATURE
<222> LOCATION: (7)..(7)
<223> OTHER INFORMATION: Xaa = DPhe

<400> SEQUENCE: 23

Xaa Xaa Asp His Arg Phe Xaa Lys
1               5

<210> SEQ ID NO 24
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 24

Tyr Asp Ala Xaa Arg Trp Asn Ala Phe Xaa Tyr
1               5                   10

<210> SEQ ID NO 25
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 25

Tyr Asp His Ala Arg Trp Asn Ala Phe Xaa Tyr
1               5                   10

<210> SEQ ID NO 26
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
```

```
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 26

Tyr Asp His Xaa Ala Trp Asn Ala Phe Xaa Tyr
1               5                   10

<210> SEQ ID NO 27
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 27

Tyr Asp His Xaa Arg Ala Asn Ala Phe Xaa Tyr
1               5                   10

<210> SEQ ID NO 28
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 28

Tyr Asp Pro Xaa Arg Trp Asn Ala Phe Xaa Tyr
1               5                   10

<210> SEQ ID NO 29
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
```

-continued

<221> NAME/KEY: MISC_FEATURE
<222> LOCATION: (10)..(10)
<223> OTHER INFORMATION: Xaa = diaminoproprionic acid (Dpr)

<400> SEQUENCE: 29

Tyr Asp Phe Xaa Arg Trp Asn Ala Phe Xaa Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (3)..(3)
<223> OTHER INFORMATION: Xaa = (rac)Atc
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 30

Tyr Asp Xaa Xaa Arg Trp Asn Ala Phe Xaa Tyr
1               5                   10

<210> SEQ ID NO 31
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 31

Tyr Asp His Pro Arg Trp Asn Ala Phe Xaa Tyr
1               5                   10

<210> SEQ ID NO 32
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = (pI)DPhe
<220> FEATURE:
<221> NAME/KEY: MISC_FEATURE
<222> LOCATION: (10)..(10)
<223> OTHER INFORMATION: Xaa = diaminoproprionic acid (Dpr)

```
-continued

<400> SEQUENCE: 32

Tyr Asp His Xaa Arg Trp Asn Ala Phe Xaa Tyr
1               5                   10

<210> SEQ ID NO 33
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DNal(2')
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 33

Tyr Asp His Xaa Arg Trp Asn Ala Phe Xaa Tyr
1               5                   10

<210> SEQ ID NO 34
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DNal(1')
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 34

Tyr Asp His Xaa Arg Trp Asn Ala Phe Xaa Tyr
1               5                   10

<210> SEQ ID NO 35
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (5)..(5)
<223> OTHER INFORMATION: Xaa = DBip
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 35

Tyr Asp His Xaa Arg Trp Asn Ala Phe Xaa Tyr
1               5                   10
```

```
<210> SEQ ID NO 36
<211> LENGTH: 11
<212> TYPE: PRT
<213> ORGANISM: Artificial Sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 36

Tyr Asp His Xaa Pro Trp Asn Ala Phe Xaa Tyr
1               5                   10

<210> SEQ ID NO 37
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 37

Tyr Asp His Xaa Lys Trp Asn Ala Phe Xaa Tyr
1               5                   10

<210> SEQ ID NO 38
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 38

Tyr Asp His Xaa Arg Pro Asn Ala Phe Xaa Tyr
1               5                   10

<210> SEQ ID NO 39
<211> LENGTH: 11
```

```
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (6)..(6)
<223> OTHER INFORMATION: Xaa = Nal(2')
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 39

Tyr Asp His Xaa Arg Xaa Asn Ala Phe Xaa Tyr
1               5                   10

<210> SEQ ID NO 40
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (6)..(6)
<223> OTHER INFORMATION: Xaa = DNal(2')
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 40

Tyr Asp His Xaa Arg Xaa Asn Ala Phe Xaa Tyr
1               5                   10

<210> SEQ ID NO 41
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (6)..(6)
<223> OTHER INFORMATION: Xaa = Bip
<220> FEATURE:
<221> NAME/KEY: MISC_FEATURE
<222> LOCATION: (10)..(10)
<223> OTHER INFORMATION: Xaa = diaminoproprionic acid (Dpr)
```

```
<400> SEQUENCE: 41

Tyr Asp His Xaa Arg Xaa Asn Ala Phe Xaa Tyr
1               5                   10

<210> SEQ ID NO 42
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (6)..(6)
<223> OTHER INFORMATION: Xaa = Tic
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 42

Tyr Asp His Xaa Arg Xaa Asn Ala Phe Xaa Tyr
1               5                   10

<210> SEQ ID NO 43
<211> LENGTH: 11
<212> TYPE: PRT
<213> ORGANISM: Artificial sequence
<220> FEATURE:
<223> OTHER INFORMATION: chimeric peptide
<220> FEATURE:
<221> NAME/KEY: MISC_FEATURE
<222> LOCATION: (2)..(10)
<223> OTHER INFORMATION: Cyclization of this peptide
<220> FEATURE:
<221> NAME/KEY: MISC_FEATURE
<222> LOCATION: (4)..(4)
<223> OTHER INFORMATION: Xaa = DPhe
<220> FEATURE:
<221> NAME/KEY: MISC_FEATURE
<222> LOCATION: (9)..(9)
<223> OTHER INFORMATION: Xaa = DPhe
<220> FEATURE:
<221> NAME/KEY: MISC_FEATURE
<222> LOCATION: (10)..(10)
<223> OTHER INFORMATION: Xaa = diaminoproprionic acid (Dpr)

<400> SEQUENCE: 43

Tyr Asp His Xaa Arg Trp Asn Ala Xaa Xaa Tyr
1               5                   10
```